United States Patent [19]

Kramer et al.

[11] 4,362,669

[45] Dec. 7, 1982

[54] URANYL COMPOUNDS EMPLOYING A STRONG BASE

[75] Inventors: George M. Kramer, Berkeley Heights; Donald M. Cox, Watchung, both of N.J.; Martin B. Dines, Santa Ana, Calif.; Edward T. Maas, Jr., Batavia, Ill.

[73] Assignee: Exxon Research and Engineering Co., Florham Park, N.J.

[21] Appl. No.: 124,306

[22] Filed: Feb. 25, 1980

[51] Int. Cl.$^3$ .................. C07F 5/00; B01D 59/34
[52] U.S. Cl. .................. 260/429.1; 204/157. 1 R; 204/158 R; 204/DIG. 11; 546/184; 546/186; 546/248; 548/402; 549/206
[58] Field of Search ............ 260/429.1, 326.8, 343.6; 546/184, 186, 248

[56] References Cited

U.S. PATENT DOCUMENTS 3,328,318  6/1967  Proops et al. .................. 260/429.1
4,243,597  1/1981  Hall et al. ..................... 260/429.1

FOREIGN PATENT DOCUMENTS 2726979  12/1978  Fed. Rep. of Germany ........ 423/19

OTHER PUBLICATIONS

Johnson, D. A., et al., J. Inorg. Nucl. Chem., vol. 41, pp. 827-831 (1979).
Kramer, G. M. et al., Inorg. Chem., vol. 20, No. 5, pp. 1418-1420 (1981).
Kramer, G. M., et al., Inorg. Chem., vol. 20, No. 5, pp. 1415-1417 (1981).
Sieck, R. F., et al.; Anal. Chem., vol. 43, No. 7, pp. 913-917 (1971).
Belford, R., et al.; J. Inorg. Nucl. Chem., vol. 14, pp. 169-178 (1960).
Zarli, B., et al.; J. Inorg. Nucl. Chem., vol. 38, No. 3, pp. 491-494.
J. C. S. Dalton; pp. 1628-1640 (1977).
Casellato, U., et al.; Inorg. Chim. Acta., vol. 18, pp. 77-112 (1976).
Schlesinger, H., et al.; J.A.C.S. vol. 75, pp. 2446-2448 (1953).
Bhattacharyya, D. C., et al.; Ind. J. Chem., vol. 13, pp. 708-710 (1975).
Mitchell, J. W., et al.; Anal. Chim Acta., vol. 57, pp. 415-424 (1971).
Subramanian, M. S., et al.; J. Inorg. Nucl. Chem., vol. 33, pp. 3001-3009 (1971).
Zarli, B., et al., J. Inorg. Nucl. Chem.; vol. 35, pp. 231-237 (1973).
Haigh, J. M., J. Inorg. Nucl. Chem.; vol. 33, pp. 1787-1797 (1971).

*Primary Examiner*—Teddy S. Gron
*Attorney, Agent, or Firm*—A. H. Krumholz

[57] ABSTRACT

Novel compositions of matter are disclosed having the general formula $UO_2AA'L_n$, in which A and A' are anions whose conjugate acids have boiling points less than about 200° C. and $pK_a$ values of 4.8 or less, L is a neutral ligand (1) having a boiling point of greater than about 200° C. and an equilibrium constant for its exchange reaction with complexed tetrahydrofuran of greater than about $10^{-3}$, or (2) having an equilibrium constant for its exchange reaction with complexed tetrahydrofuran of greater than about $10^3$, and n is an integer of from 1 to 4.

21 Claims, No Drawings

URANYL COMPOUNDS EMPLOYING A STRONG BASE

BACKGROUND OF THE INVENTION

The present invention relates to compositions of matter containing the uranyl ion. More specifically, the present invention relates to such compositions of matter which are highly useful in uranium isotope separation processes.

Over the past few years, a significant search has been made for the discovery of volatile uranyl compounds which can be used for the separation of isotopes. Such a process and compounds useful therein are disclosed in copending application Ser. No. 865,963 filed on Dec. 30, 1977 in the names of Martin B. Dines, et al., and a number of specific compounds useful in that process are similarly disclosed in U.S. patent application Ser. No. 868,450 filed on Jan. 10, 1978 in the names of Richard B. Hall et al. now abandoned. The principal compounds disclosed in those applications have the general formula $UO_2(1,1,1,5,5,5$ hexafluoro-2,4-pentanedionate$)_2.L$, where L is a neutral ligand such as tetrahydrofuran and others, such as ethanol or N,N-dimethylformamide which are listed in those patent applications. In a subsequent application given Ser. No. 961,363 and filed on Nov. 16, 1978, now U.S. Pat. No. 4,243,597, Messrs. Hall et al. disclose compounds having the general formula $UO_2AA'L_n$ where n is 0 or 1, A and A' are anions whose conjugate acids have boiling points less than about 200° C. and $pK_a$ values of 4.8 or less, and where L is a neutral ligand having a boiling point less than about 190° C. and an equilibrium constant for its exchange reaction with the complexed tetrahydrofuran of between about $10^{-3}$ and $10^3$.

All of these compounds have been found to be particularly useful in such isotope separation processes precisely because they are relatively volatile uranyl ion-containing compounds, and they also have isotopically shifted infrared absorption spectra associated therewith. Therefore, by irradiating these compounds in the vapor phase with infrared radiation which is preferentially absorbed by molecular vibrations of molecules containing a predetermined isotope of the element which is to be separated, excited molecules enriched in that isotope can be separated therefrom. In particular, the compounds disclosed are highly significant in that they possess infrared absorptions which exhibit isotopic shifts within the range of the wavelength of commercially available $CO_2$ lasers.

In the background section of U.S. patent application Ser. No. 865,963, a number of references teaching various compounds having the general formula $UO_2(\beta$-diketonate$)_2.L$ where L is a neutral ligand, are disclosed. These include U.S. patent application Ser. No. 662,600 of Messrs. Schlessinger and Brown published in the Official Gazette on Mar. 6, 1951, Chemical Abstracts, 46, 10192b, as well as those same authors' subsequent publication in the Journal of the American Chemical Society, 75, pages 2446-8 (1953) in which they disclose $UO_2(1,1,1$-trifluoro-2,4-pentanedionate$)_2$ having the highest vapor pressure for any of the uranyl β-diketonates which they studied, namely about 0.0027 torr at 130° C.

In the aforesaid application of Messrs. Dines et al., reference is also made to a comprehensive review of the properties of various uranyl compounds with chelating ligands, namely Casellato et al., in Inorganica Chemica Acta, 18, 77-112 (1976). In that article the behavior of the actinides in their various oxidation states and combined with various organic chelating ligands such as the β-diketones, is discussed in detail. The majority of the anions disclosed in that article, however, have conjugate acids which have $pK_a$ values considerably higher than 4.8. These include disclosures of compounds of the general formula $UO_2(A)_2.L$, where A is tropolonate, acetylacetonate, and the amine of dibenzoylmethane, thenoyltrifluoroacetone, benzoylacetone, trifluoroacetone, etc.

Reference is also made in the Dines et al. application to Subramanian et al., "Complexes of Uranyl β-Diketones with Aromatic Amine N-Oxides," Journal of Inorganic Nuclear Chemistry, 33, 3001 (1971) which discusses a number of compounds of the general formula $UO_2(1,1,1,5,5,5,$-hexafluoroacetylacetonate$)_2L$, where the ligands, L, are various amine N-oxides, such as pyridine N-oxide. It is also noted that the same types of compounds, but where L is a sulfoxide, such as dibutyl sulfoxide, or a phosphine oxide, are disclosed in articles such as Sieck, "Gas Chromatography of Mixed-Ligand Complexes of the Lanthanides and Related Elements" submitted for his Ph.D. thesis, Iowa State University, 1971 and two other articles by Sieck in Chemical Abstracts, 75, 147395Q and Nuclear Science Abstracts, 25, (17), 39410 (1971). Also Mitchell (Synergic Solvent Extraction and Thermal Studies of Fluorinated Beta-Diketone-Organophosphorous Adduct Complexes of Lanthanide and Related Elements, Ph.D. Thesis, Iowa State University, 1970) prepared the tributylphosphate complex of $UO_2$(hfacac$)_2$, where (hfacac) is the 1,1,1,5,5,5 hexafluoro-2,4-pentanedionate anion, and showed that it vaporized at about 150° C.

In co-pending application, Ser. No. 961,363, now U.S. Pat. No. 4,243,597, Messrs. Hall, Kaldor, Kramer and Dines disclose a number of volatile uranyl compounds, including those having the general formula $UO_2AA'L_n$, where A and A' are certain selected anions and L is again a neutral ligand. Both of the above-noted co-pending applications of Messrs. Dines et al. and Hall et al. discuss an article by Belford et al. (J. Inorg.Nucl.-Chem. 14 169 (1960)) in which the authors describe their preparation of $UO_2$(hfacac$)_2$.4$H_2O$, which they describe as decomposing upon heating above 58° C. This article then goes on to discuss the infrared absorption bands for various uranyl compounds, and the effect of ligand substitution on the visible spectra, concluding that the more basic ligands attach more securely to the uranium atom, thus decreasing its coordinating tendencies.

A number of references have also discussed compounds variously described as uranyl phthalocyanine (Bloor et al., Canadian Journal of Chemistry, 42, 2201-2208 (1964)), said to be sublimable under a vacuum "below 0.01 mm pressure at 400°-450° C." and uranyl superphthalocyanine (Day, Marks and Wachter, "Large Metal Ion-Centered Template Reactions. A Uranyl Complex of Cyclopentakis (2-iminoisoindoline)": J.A.C.S., 97:16, Aug. 6, 1975, 4519-4527). Furthermore, U.S. Pat. No. 4,097,384 to Messrs. Coleman and Marks discloses the possible laser irradiation of that compound, as well as other possible uranyl compounds. The Day, Marks and Wachter paper was presented orally at the American Crystallographic Association meeting in Berkeley, Calif. in March of 1974, as well as at the American Chemical Society meeting in Los Angeles in April of 1974. In a later paper entitled "Large Metal Ion-Centered Template Reactions. Chemical and Spectral Studies of 'Superphthalocyanine' Dioxocyclopentakis (1-iminoisoindolinato) Uranium (VI) and Its Derivatives," Messrs. Marks and Stojakovic, *J. Amer. Chem. Soc.*, 100, page 1695 (March 1978), further discuss this compound and indicate that a product can be obtained by sublimation at 400° C.

In an article entitled "Volatile Complexes of Some Lanthanides and Related Elements with Fluorinated Beta-Diketones and Organophosphorous Adducts," *Anal. Chim. Acta*, 57, 415–424 (1971), Mitchell et al. discuss the use of various bases to displace the water of hydration from chelates of the lanthanides with trifluoroacetylacetone and hexafluoroacetylacetone. They thus employ tri-n-butyl phosphate in compounds having the general formula M(A)$_3$.2TBP, M being one of a number of lanthanide elements. They note that these compounds were considerably more volatile and thermally stable than the corresponding hydrated chelates and conclude that the " . . . water of hydration is instrumental in the thermal degradation of chelates of the rare earths with $\beta$-diketones."

In a series of articles by Levy et al. and Taylor et al., *J.C.S. Dalton*, 1628–1640 (1977) the authors discuss their studies of UO$_2$(hexafluoropentane-2,4-dionato)$_2$(trimethylphosphate). The final articles in this series discuss the structure of the polymorphs of this compound.

Finally, in an article by Messrs. Johnson, Taylor and Waugh, *J. Inorg. Nucl. Chem.*, Vol. 41, pages 827–831 (1979) the authors discuss the compound UO$_2$(hfacac)$_2$NH$_3$.

SUMMARY OF THE INVENTION

In accordance with the present invention, an entire class of compositions of matter have now been discovered for use in connection with the separation of isotopes. It has thus been discovered that this class of uranyl ion-containing molecules, although non-volatile are particularly useful in connection with isotope separation processes by exhibiting an unexpectedly narrow line width of less than about 10 cm$^{-1}$, and in many cases less than about 6 cm$^{-1}$. In addition, the frequency of the $\nu_3$ absorption band is dependent upon the base strength of the neutral ligand L in compounds of the general formula UO$_2$AA'L$_n$, and this permits one to select a compound having an absorption band which coincides with the emission of a CO$_2$ laser, for example. Of a further unexpected nature is the fact that you can substantially change the absorption frequency of these compounds by changing the neutral ligand L, without necessarily increasing the bandwidth, as would have been expected. For example, the emission of a CO$_2$ laser has a peak at about 956 cm$^{-1}$, and the following neutral ligands L provide the following gas phase absorption maximum for the compounds UO$_2$AA'L, as well as the following bandwidths:

| Ligand | Gas Phase Absorption Maximum, (cm$^{-1}$) | Bandwidth, (FWHM,m$^{-1}$) |
|---|---|---|
| hexamethylphosphoramide | 950.6 | approx. 5 |
| triethylphosphineoxide | 951.6 | approx. 5 |
| pyridine N—oxide* | 954.5 | approx. 6 |
| trimethyl phosphate* | 954.6 | approx. 5 |
| tetrahydrofuran** | 956 | approx. 8 |

-continued

| Ligand | Gas Phase Absorption Maximum, (cm$^{-1}$) | Bandwidth, (FWHM,m$^{-1}$) |
|---|---|---|
| acetone** | 959.5 | approx. 5 |

*these compounds are disclosed in the prior art
**these compounds are disclosed in previously filed U.S.Pat. application Ser. No. 961,363

It is noted that some of the ligands noted above are disclosed in the prior art, while others are disclosed in previously filed patent applications of others. The point is, however, that utilizing either the compounds of the present invention or those of the prior art, it is possible to select a $\nu_3$ band which corresponds with different emission levels of a laser such as a CO$_2$ laser by selecting the neutral ligand L, again without increasing the bandwidth by doing so. Furthermore, the unexpected narrowness of the bandwidth of this absorption band increases the selectivity of an isotope separation process employing these compounds.

The compositions of matter according to the present invention comprise novel uranyl ion-containing molecules having the general formula UO$_2$AA'L$_n$, in which A and A' are anions whose conjugate acids have boiling points of less than about 200° C. and pK$_a$ values of 4.8 or less, L is a neutral ligand either (1) having a boiling point of greater than about 200° C. and an equilibrium constant for its exchange reaction with the complexed tetrahydrofuran of greater than about 10$^{-3}$, or (2) having an equilibrium constant for its exchange reaction with the complexed tetrahydrofuran of greater than about 10$^3$, the equilibrium being measured in chloroform, and n is an integer from 1 to 4, preferably 1. It is thus noted that when the neutral ligand has a boiling point of greater than about 200° C. somewhat lower base strengths can be tolerated, but on the other hand when the relative base strength of other compounds, i.e., as measured by the equilibrium constant for exchange with tetrahydrofuran, are significantly greater, then the boiling point of the neutral ligand can be somewhat lower. In any event, the neutral ligand L will most preferably be selected from the group consisting of primary, secondary and tertiary amines, alkylamineoxides, amides, aldehydes, ketones, ethers, esters, imides, alkenyl carbonates, lactones and phosphorous compounds having the formula

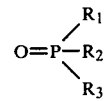

where R$_1$, R$_2$ and R$_3$ can be alkyl, N-alkyl amino, and N—N dialkyl amino groups. In addition, in the case of a neutral ligand L having an equilibrium constant for its exchange reaction with the complexed tetrahydrofuran of greater than about 10$^3$, the neutral ligand L can also comprise dialkylsulfoxides in which the alkyl group includes from 1 to 3 carbon atoms.

In case (1) above where the neutral ligand L has a boiling point of greater than about 200° C. and an equilibrium constant for its exchange reaction with the complexed tetrahydrofuran of greater than about 10$^{-3}$, the equilibrium constant for its exchange reaction with the complexed tetrahydrofuran may be, for example, between about $10^{-3}$ and $10^9$, and preferably greater than about $10^3$.

In accordance with the embodiment of the present invention where the neutral ligand L is an amide, it can comprise compounds such as N-methyl acetamide or alkyl substituted ureas, such as tetralkyl ureas, in particular tetramethyl urea. Further in accordance with this embodiment where the neutral ligand L comprises the above-noted phosphorous compound, it will preferably comprise a trialkylphosphineoxide such as triethylphosphineoxide, or a hexalkylphosphoramide such as hexamethylphosphoramide.

In another aspect of this embodiment of the present invention where the neutral ligand L comprises a secondary amine, it will preferably comprise pyrollidine or imidazole.

In accordance with case (2) above in which the neutral ligand L has an equilibrium constant for its exchange reaction with the complexed tetrahydrofuran of greater than about $10^3$, that equilibrium constant will preferably be greater than about $10^4$, such as between about $10^4$ and $10^9$.

In a preferred embodiment of this aspect of the present invention the neutral ligand will again have a boiling point of greater than about 200° C.

In accordance with one aspect of this embodiment of the present invention, where the above-noted amines are employed as the neutral ligand L, they will preferably comprise alkyl amines, such as methylamine, ethylamine and propylamine, piperidine, and alkyl substituted piperidine.

In another aspect of this embodiment of the present invention, in which the above-noted dialkylsulfoxides are employed, they will preferably comprise dimethylsulfoxide.

In accordance with either of these embodiments of the present invention, the anions A and A' can be monodentate or polydentate, but preferably they will be bidentate. In a preferred embodiment, the anions A and A' will be highly fluorinated, and most preferably they will both comprise the 1,1,1,5,5,5-hexafluoro-2,4-pentanedionate ion, or will be completely fluorinated.

DETAILED DESCRIPTION

The uranyl ion-containing compounds of the present invention must contain anions having a total net charge of $-2$ so that a neutral complex is formed. Furthermore, these compounds include anions and/or ligands which occupy all of the available sites in the first coordination shell of the uranyl ion in order to minimize the intermolecular electrostatic attraction between one uranyl ion and the anions or ligands surrounding another uranyl ion. As for the anions themselves, they are polydentate, and will form a chelation ring around a portion of the uranyl ion. However, as set forth above, it is also possible for n to be an integer greater than 1, e.g., from 2 to 4. In that case it is believed, without being limited thereto, that the ligands are closely bound to the uranyl moiety in a specific geometric configuration.

The anions of the present invention are selected so as to effectively enhance the Lewis acidity of the complexed uranyl ion. This is best accomplished by employing electronegative elements such as fluorine in connection with these anions to inductively withdraw electron density from the uranyl ion leading to the formation of more ionic bonds. Thus in cases where a neutral ligand is employed, such as where a pair of bidentate anions occupy four of the available sites in the first coordination shell of the uranyl ion, the ability of the uranyl ion to bond with strong Lewis bases such as those containing oxygen and nitrogen atoms is increased. These bases are the neutral ligands L referred to above, and there is of course a reciprocal interaction between the ability of the uranyl ion to combine with the anions and the neutral ligand or base L.

In the case of the anions A and A' in the compounds of this invention their ability to stabilize the complexes of the present invention is directly related to the acidity of their conjugate acids, which can be measured by their acid dissociation constants in water.

As for the acidity of these conjugate acids, in order to be useful in the compositions of the present invention, it has also been found that these conjugate acids must have $pK_a$ values of 4.8 or less. That is, these acids must be about at least as strong as trifluoroacetylacetone, which has a $pK_a$ value of about 4.7. It is preferred that these anions be polydentate and have an atomic framework exhibiting a minimum bite or distance between coordinating functionalities of the diketonate unit so as to sterically minimize the attack of various basic components in solution on the uranium atom. Thus, chelate rings would be formed containing preferably 5 or 6 members, and this will provide preferred shielding and will be much less strained than those with 3 or 4 members. They will therefore also be less likely to open and bridge to other uranyl ions. Thus, small chelating ions like nitrate or acetate ions would not be suitable candidates for the anionic reagents in the compounds of the present invention.

Preferable anions for use in connection with the compounds of the present invention will thus include, in addition to the hexafluoroacetylacetonate anion discussed above, trifluoroacetylacetonate ($CF_3OCH$-$COCH_3$), 3-trifluoroacetyl-1,1,1,5,5,5-hexafluoro-2,4-pentanedionate (($CF_3CO)_3C$), 3-fluoro-1,1,1,5,5,5-hexafluoroacetylacetonate ($(CF_3CO)_2CF$), 1,1,1,2,2,3,3,7,7,7-decafluoro-4,6-heptanedionate ($CF_3COCHCOC_3F_7$), and 1,1,1,2,2,6,6,7,7,7-decafluoroheptane-3,5-dionate, as well as fluorinated tropolonates, such as

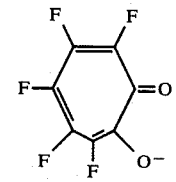

The neutral ligand L of the present invention must also meet certain criteria. As set forth above, these include either (1) a boiling point of greater than about 200° C., at 1 atmosphere pressure and a minimum basicity requirement as set forth herein or (2) a more stringent basicity requirement. In particular, all of these ligands are highly basic and thus form very strong bonds between the ligand L and the uranyl ion itself. The basicity requirements set forth above for these ligands may thus be defined in terms of the molecule $UO_2(hfacac)_2 \cdot THF$. That is, the neutral ligand L will have a basicity measured by the equilibrium constant for the following reaction:

Thus, in the case where the neutral ligands L of the present invention have boiling points greater than about 200° C., they may have K's which are greater than about $10^{-3}$, such as between about $10^{-3}$ and $10^9$ and preferably greater than about $10^3$. On the other hand, irrespective of the boiling point of the ligand L employed, such ligands can be utilized which yield an equilibrium constant K of greater than about $10^3$, and preferably greater than about $10^4$ such as between about $10^4$ and $10^9$.

The principal requirement for the overall compounds according to the present invention includes the fact that they form monomeric species in solution, and as is further set forth above they exhibit infrared characteristics such that the uranyl asymmetric stretch at about 950 $cm^{-1}$ will be characterized with an FWHM or half width of less than about 10 $cm^{-1}$, preferably less than about 6 $cm^{-1}$.

In accordance with the above requirements for the neutral ligands L hereof, the compounds meeting these prerequisites can include the primary, secondary and tertiary amines, alkylamineoxides, amides, aldehydes, ketones, ethers, esters, imides, alkenyl carbonates, lactones and phosphorous compounds having the general formula

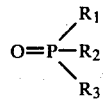

where $R_1$, $R_2$ and $R_3$ are alkyl, N-alkylamine, and/or N—N dialkylamino groups.

Thus, in the case where the neutral ligand L has a boiling point of greater than about 200° C. and an equilibrium constant for its exchange reaction with the complexed tetrahydrofuran of greater than about $10^{-3}$, preferred compounds include N-methylacetamide, alkyl substituted ureas, such as tetralkylureas, in particular tetramethylurea, alkenyl carbonates, such as propylene carbonate (4,methyl-1,3 dioxolan-2-one) and ethylene carbonate, and substituted or unsubstituted lactones, such as $\gamma$-valerolactone and $\gamma$-butyrolactone. Also, in accordance with this embodiment it is preferred that the above phosphorous compound comprise trialkylphosphineoxides, such as triethylphosphineoxide and tributylphosphineoxide, or hexalkylphosphoramides, such as hexamethylphosphoramide. A preferred secondary amine in accordance with this embodiment of the invention will be pyrrolidine.

On the other hand, in accordance with the embodiment of this invention where the neutral ligand L has an equilibrium constant for its exchange reaction with the complexed tetrahydrofuran of greater than about $10^3$, preferred primary secondary and tertiary amines comprise the alkylamines, such as trimethylamine, triethylamine, and tripropylamine, piperidine, and alkyl substituted piperidine.

Also in accordance with this embodiment of the present invention the neutral ligand L can also comprise dialkylsulfoxides where the alkyl groups include from 1 to 3 carbon atoms, preferably dimethylsulfoxide.

As for the methods of actually preparing the preferred compositions of the present invention, these are as set forth in pending U.S. patent application Ser. No. 961,363 filed on Nov. 16, 1978, in the names of Richard B. Hall et al., now U.S. Pat. No. 4,243,597. Those methods are set forth beginning on page 16 of that application, and continuing through to page 19 thereof, and that disclosure is specifically incorporated herein by reference thereto. While the methods so disclosed, including the use of $UO_2Cl_2$ and $UO_2(NO_3)_2.6H_2O$ as starting materials and sources of the $UO_2$ ion, the specific neutral bases of the present invention must of course be substituted for the neutral bases shown therein in order to prepare the compounds of the present invention.

As set forth above the novel uranyl ion-containing compounds of this invention can include more than one ligand L. For example, where L is hexamethylphosphoramide, n can be 2 or 4 and stable compounds can be prepared. These compounds can be produced, for example, by producing the complexes in the presence of excess ligand, or by producing the compounds where $n=1$, and then adding the ligand to a solution thereof. All of the compounds of this invention can be employed in processes for the separation of uranium isotopes. For example, they can be employed in such processes where these compounds are irradiated by means of a laser, such as a $CO_2$ laser, the compounds being contained in a rapidly moving stream formed by expanding a gaseous mixture or a solution of the compounds through a nozzle. Such a process is shown in U.S. Pat. No. 4,025,790, in which a molecular gas of the compound ($UF_6$ in that case) is formed into a stream and is then cooled by adiabatic expansion in a nozzle, prior to excitation of these molecules by means of a laser. As is further shown in that patent, whose disclosure regarding such a nozzle containing-process for isotope separation is incorporated herein by reference thereto, baffles are employed to peal off the edge regions of the cooled gas exiting the nozzle so that the width of the velocity distribution and the Doppler width of the absorption lines are reduced.

We claim:

1. A composition of matter having the formula $UO_2AA'L_n$, wherein A and A' are anions whose conjugate acids having boiling points of less than about 200° C. and $pK_a$ values of 4.8 or less, and which form chelate rings having more than four members, L is a neutral ligand having a boiling point of greater than about 200° C. and an equilibrium constant for its exchange reaction with the complex of $UO_2AA'$ with tetrahydrofuran of greater than about $10^{-3}$, said neutral ligand being selected from the group consisting of primary, secondary and tertiary amines, alkylamineoxides, amides, aldehydes, ketones, lactones, ethers, esters, imides, alkenyl carbonates and phosphorous compounds having the formula

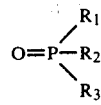

wherein $R_1$, $R_2$ and $R_3$ are selected from the group consisting of ethyl, N-alkylamino, and N,N-dialkylamino groups, and n is an integer from 1 to 4, said composition forming a monomeric species in solution and exhibiting an infrared band at about 950 $cm^{-1}$ having a bandwidth of less than about 10 $cm^{-1}$.

2. The composition of matter of claim 1 wherein n is 1.

3. The composition of matter of claim 1 or 2, wherein said equilibrium constant for its exchange reaction with the complex of $UO_2AA'$ with tetrahydrofuran is greater than about $10^3$.

4. The composition of matter of claim 1 or 2, wherein said equilibrium constant for exchange reaction with the complex of $UO_2AA'$ with tetrahydrofuran is between about $10^{-3}$ and $10^9$.

5. The composition of matter of claim 1 or 2, wherein said anions A and A' comprise the same anion.

6. The composition of matter of claim 5, wherein said anions comprise the 1,1,1,5,5,5 hexafluoro-2,4-pentanedionate anion.

7. The composition of matter of claim 1 or 2, wherein said amide is selected from the group consisting of N-methyl acetamide and alkyl substituted ureas.

8. The composition of matter of claim 7, wherein said alkyl substituted urea comprises tetralkyl urea.

9. The composition of matter of claim 1 or 2, wherein said phosphorous compounds comprise a hexaalkylphosphoramide.

10. The composition of matter of claim 9, wherein said phosphorous compound comprises hexamethylphosphoramide.

11. The composition of matter of claim 1 or 2, wherein said secondary amine comprises pyrrolidone.

12. The composition of matter of claim 1 or 2, wherein said alkylamineoxide comprises trimethylamine oxide.

13. A composition of matter having the formula $UO_2AA'L_n$, wherein A and A' are anions whose conjugate acids have boiling points of less than about 200° C. and $pK_a$ values of 4.8 or less, and which form chelate rings having more than four members, L is a neutral ligand having an equilibrium constant for its exchange reaction with the complex of $UO_2AA'$ with tetrahydrofuran of greater than about $10^3$, said neutral ligand being selected from the group consisting of primary, secondary and tertiary amines, alkylamineoxides, amides, aldehydes, ketones, ethers, esters, imides, alkenyl carbonates, lactones, dialkylsulfoxides wherein said alkyl groups include from 2 to 3 carbon atoms, and phosphorous compounds having the formula

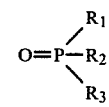

wherein $R_1$, $R_2$ and $R_3$ are selected from the group consisting of alkyl, N-alkylamino, and N,N-dialkylamino groups and n is an integer from 1 to 4, said composition forming a monomeric species in solution and exhibiting an infrared band at about 950 $cm^{-1}$ having a bandwidth of less than about 10 $cm^{-1}$.

14. The composition of matter of claim 13 wherein n is 1.

15. The composition of matter of claim 13 or 14, wherein said equilibrium constant for its exchange reaction with the complex of $UO_2AA'$ with tetrahydrofuran is greater than about $10^4$.

16. The composition of matter of claim 13 or 14, wherein said equilibrium constant for its exchange reaction with the complex of $UO_2AA'$ with tetrahydrofuran is between $10^4$ and $10^9$.

17. The composition of matter of claim 13 or 14, wherein said neutral ligand has a boiling point of greater than about 200° C.

18. The composition of matter of claim 13 or 14, wherein said primary, secondary and tertiary amines are selected from the group consisting of the alkyl amines, piperidine, and alkyl substituted piperidine.

19. The composition of matter of claim 13 or 14, wherein said anions A and A' comprise the same anion.

20. The composition of matter of claim 19, wherein said anion comprises 1,1,1,5,5,5 hexafluoro-2,4-pentanedionate anions.

21. The composition of matter of claim 18, wherein said alkyl amines are selected from the group consisting of trimethylamine, triethylamine and tripropylamine.

* * * * *